US006340024B1

(12) United States Patent
Brookman et al.

(10) Patent No.: US 6,340,024 B1

(45) Date of Patent: Jan. 22, 2002

(54) PROTECTIVE HOOD AND ORAL/NASAL MASK

(75) Inventors: Michael J. Brookman, Davie; Eric M. Hiner, Plantation, both of FL (US)

(73) Assignee: DME Corporation, Ft. Lauderdale, FL (US)

( * ) Notice: Subject to any disclaimer, the term of this patent is extended or adjusted under 35 U.S.C. 154(b) by 0 days.

(21) Appl. No.: 08/334,751

(22) Filed: Nov. 4, 1994

Related U.S. Application Data

(63) Continuation of application No. 08/001,339, filed on Jan. 7, 1993, now abandoned.

(51) Int. Cl.[7] ........................ A61M 16/00; A61M 16/22

(52) U.S. Cl. ............................ 128/201.25; 128/201.15; 128/201.19; 128/201.22; 128/201.23; 128/201.24; 128/201.26; 128/201.28; 128/204.18; 128/205.25; 128/205.26; 128/205.27; 128/205.28; 128/205.29; 128/206.12; 128/206.17

(58) Field of Search ........................ 128/201.15, 201.19, 128/201.22–201.26, 201.28, 204.18, 205.25–205.29, 206.12, 206.17

(56) References Cited

U.S. PATENT DOCUMENTS

| | | | | |
|---|---|---|---|---|
| 128,451 | A | 7/1872 | Ackerman | |
| 533,854 | A | 2/1895 | Loeb | |
| 923,776 | A | 6/1909 | Danielewicz | 128/205.28 |
| 1,196,539 | A | 8/1916 | Goldberg | |
| 1,410,928 | A | 3/1922 | Knoblock | |
| 1,889,015 | A | 11/1932 | Davis | |
| 1,894,266 | A | 1/1933 | Durgin et al. | |
| 1,929,343 | A | 10/1933 | Belloni | |
| 2,048,059 | A | 7/1936 | Giraudet de | |
| 2,435,167 | A | 1/1948 | Stetson | |
| 2,445,478 | A | 7/1948 | Foster et al. | |
| 2,484,269 | A | 10/1949 | Carlson | |
| 2,683,876 | A | 7/1954 | Sullivan | |
| 2,821,192 | A | 1/1958 | Monro | |
| 2,988,749 | A | 6/1961 | Crouzet | |
| 3,017,888 | A | 1/1962 | Weiner | |
| 3,072,119 | A | 1/1963 | Matheson | |
| 3,181,532 | A | 5/1965 | Harris | |
| 3,216,415 | A | 11/1965 | Littleton | |
| 3,295,522 | A | 1/1967 | Johnson | |
| 3,381,454 | A | 5/1968 | Sponsel | |
| 3,385,293 | A | 5/1968 | Phillips | |

(List continued on next page.)

FOREIGN PATENT DOCUMENTS

| | | | |
|---|---|---|---|
| CA | 1326805 | 2/1994 | |
| EP | 0086871 | 8/1983 | |
| EP | 0327643 B1 | 10/1994 | |
| GB | 897531 | 5/1962 | |
| WO | 8701949 | 4/1987 | 128/205.12 |
| WO | 8900873 | 2/1989 | 128/205.12 |

*Primary Examiner*—John G. Weiss
*Assistant Examiner*—Mital Patel
(74) *Attorney, Agent, or Firm*—Malin, Haley & DiMaggio, P.A.

(57) ABSTRACT

An improved oral/nasal mask-hood is provided for protection of individuals in the event of fire or smoke exposure. When attached to a supplemental supply of oxygen the mask-hood also provides hypoxia protection to individuals exposed to decompression as in some aircraft incidents. The mask-hood employs a five stage filtering process for converting toxic atmospheric air to breathable fresh air. The hood covers the wearer's head, neck and shoulder area. A neck seal is provided inside the hood for preventing gases from locating within the hood and irritating the wearer's eyes. A transparent member is located on the hood adjacent the wearer's line of sight to provide visibility during the emergency. The hood-mask device, as assembled, is small enough to retrofit into the space provided for the present decompression mask alone.

19 Claims, 5 Drawing Sheets

U.S. PATENT DOCUMENTS

| | | | |
|---|---|---|---|
| 3,458,864 A | 8/1969 | Austin et al. | |
| 3,545,437 A | 12/1970 | Quackenbush | |
| 3,562,813 A | 2/1971 | Origer | |
| 3,565,068 A | 2/1971 | Bickford | |
| 3,650,269 A | 3/1972 | Curtis | |
| 3,762,407 A | 10/1973 | Shonerd | |
| 3,838,462 A | 9/1974 | Barbeau et al. | |
| 3,906,945 A | 9/1975 | Netteland et al. | |
| 3,910,252 A | 10/1975 | Richard | |
| 3,925,248 A | 12/1975 | Moroni et al. | |
| 3,951,160 A | 4/1976 | Nitu | |
| 4,005,708 A | 2/1977 | Netteland et al. | |
| 4,026,296 A | 5/1977 | Stoy et al. | |
| 4,039,620 A | 8/1977 | Netteland et al. | |
| 4,098,271 A | 7/1978 | Maddock | |
| 4,099,526 A | 7/1978 | Mascher | |
| 4,116,237 A | 9/1978 | Birch | |
| 4,126,131 A | 11/1978 | Davis et al. | |
| 4,188,947 A | 2/1980 | Pasternack | |
| 4,207,883 A | 6/1980 | Shindler | |
| 4,231,118 A | 11/1980 | Nakagawa | |
| 4,236,514 A | 12/1980 | Moretti | |
| 4,239,638 A | 12/1980 | Beretta et al. | |
| 4,266,301 A | 5/1981 | Canda | |
| 4,314,566 A | 2/1982 | Kiwak | |
| 4,440,163 A | 4/1984 | Spergel | |
| 4,473,072 A | 9/1984 | Walther | |
| 4,484,575 A | 11/1984 | Brockway et al. | |
| 4,502,480 A | 3/1985 | Yamamoto | |
| 4,513,053 A | 4/1985 | Chen et al. | |
| 4,517,685 A | 5/1985 | Lesley | |
| 4,533,367 A | 8/1985 | Hadzismajlovic | |
| 4,552,140 A | 11/1985 | Crowley et al. | |
| 4,554,683 A | 11/1985 | Wong | |
| 4,559,939 A | 12/1985 | Levine et al. | |
| 4,572,178 A | 2/1986 | Takase et al. | |
| 4,573,464 A | 3/1986 | Yo | |
| 4,583,535 A | 4/1986 | Saffo | 128/201.25 |
| 4,586,500 A | 5/1986 | Glynn | |
| 4,619,254 A | 10/1986 | Moretti et al. | |
| 4,623,520 A | 11/1986 | Robinet | |
| 4,627,431 A | 12/1986 | Werjefelt | |
| 4,637,383 A | 1/1987 | Lopez | |
| 4,643,182 A | 2/1987 | Klein | |
| 4,665,910 A | 5/1987 | Kolbe et al. | |
| 4,671,268 A | 6/1987 | Hunt | |
| 4,671,270 A | 6/1987 | Kato | |
| 4,683,880 A | 8/1987 | Werjefelt | |
| 4,696,338 A | 9/1987 | Jensen et al. | |
| 4,754,751 A | 7/1988 | Mausteller et al. | 128/205.28 |
| 4,807,614 A | 2/1989 | van der Smissen | |
| 5,003,974 A | 4/1991 | Mou | 128/205.12 |
| 5,038,768 A | 8/1991 | McGoff et al. | 128/205.12 |
| 5,115,804 A | 5/1992 | Brookman | 128/201.22 |

PROTECTIVE HOOD AND ORAL/NASAL MASK

This application is a continuation of U.S. application Ser. No. 08/001,339, filed Jan. 7, 1993, now abandoned.

BACKGROUND OF THE INVENTION

1. Field of the Invention

The present invention relates generally to protection during hypoxia and fire emergencies and more particularly is concerned with a protective hood and oral/nasal mask for providing breathable air during hypoxia and fire emergencies.

2. Description of the Prior Art

In aircraft fire situations, toxic and noxious gases are typically present in the aircraft. Survivors of recent aircraft fires have stated that one or two breaths of the smoke and noxious gases present in the aircraft fire resulted in the passengers lungs feeling solidified and in the passengers experiencing extreme sleepiness. Passengers of aircraft fires cannot risk taking several breaths of the contaminated, toxic atmospheric air prior to receiving purified air when such immediate and critical symptoms occur from one or two breaths of the noxious and toxic gases. In addition, the noxious gases which are present tend to immediately irritate the passengers eyes, preventing the passenger from seeing and being able to find emergency exits. Also, if the emergency tends to last for an extended period of time, the existent oxygen supplies on the aircraft can be depleted. Many aircraft are equipped with emergency masks for use in case of aircraft decompression. These masks are designed to provide oxygen to air craft occupants very quickly. The present invention combines this hypoxia protection with smoke and fire protection in a single device. The standard hypoxia device provides supplemental oxygen to support respiration but still relies on the aircraft cabin air for additional quantities of air.

PCT International Application No. WO 89/00873 to Brookman discloses a small dropout package containing a protective hood for deployment to enclose the head of the passenger to improve the passenger's vision in the smoke, a protectable breathing mask for enclosing the mouth and nose of the passenger in order to provide breathable air and a dual air supply system. The Brookman device provides a chemical air purifier having a wet scrubbing system for purifying cabin air of contaminants to supply breathable air to the user.

Brookman discloses using a wet filtering system. The filtering system of Brookman contains a first chamber which contains a sac to store wet base materials until activated by pulling on an actuator. Once activated, the wet base materials scrub the acid gases, which have entered the first chamber, to neutralize such gases. The neutralized gases are then allowed to passed on through a porous membrane to a second chamber having a catalyst disposed within the second chamber. The porous membrane, however, retains the wet base materials within the first chamber. The wet base materials are released from the sac by the pull of a cord which pulls the sac between a pair of rollers to rupture the sac and displace the wet chemical agent into the first chamber.

The use of the wet filtering system taught by the Brookman reference creates several significant disadvantages and problems during operation of such filtering system. The first disadvantage is the mechanical process required to rupture the sac to release the wet chemical agent. The pulling of the sac is achieved by a cord which is attached at both ends. If either end of the cord is inadvertently or accidently disconnected, the sac will not be ruptured and the wet chemical agent will not be released. Thus, the toxic and noxious gases passing in the first chamber will not be neutralized, but sent to the second chamber in their original harmful state. Additionally, as a liquid scrubber will be released in the first chamber upon rupture of the sac, an additional sealing means has to provided at the rollers to prevent leakage of the liquid out of the first chamber. Such leakage would again allow the gases to pass through the first chamber unneutralized. Another problem with the use of liquid scrubber is that during fire emergencies, concerning high temperatures, there will be concerns regarding the boiling points of the liquid used to neutralize the gases. All of these problems with the filtering system of the Brookman create significant safety concerns during real emergencies. Brookman also fails to provide for a heat absorber. Accordingly, the gas which travels through the catalyst can be at a high and harmful temperature and could cause serious injury to the user of such device.

PCT International Application No. WO 87/01949 to Stewart discloses a breathing apparatus comprising a face mask attached to but detachable from an oxygen supply tube and connected to an inflatable reservoir or bag held in a deflated rolled up condition but releasable to provide when attached and deflated, an oxygen supply system and, when detached and inflated a portable respirator or ventilator in a closed rebreathing system with rebreathing bag and oxygen supply in a microclimate free from noxious or hot gases.

Atmospheric air is prevented from entering the Stewart device, as the Stewart device is merely connected to an oxygen supply. Another disadvantage of Stewart, is the hood fails to provide a protective neck seal, as the reference discloses providing goggles to protect the eyes from noxious gases and very hot air.

Brookman and Stewart both fail to disclose a desiccant material for eliminating fogging which could affect the user's visibility. In Stewart, the exhaled air passes through a carbon dioxide absorber and inflates the reservoir which becomes a rebreathing bag. The carbon dioxide absorber, extends the time for which rebreathing can take place without dangerous build of carbon dioxide. The carbon dioxide absorber does not acts as an anti-fogging device. In fact, the carbon absorber operates regardless of whether the Stewart device is utilized with a hood or not and is, thus, not attached to the hood.

U.S. Pat. No. 4,583,535 issued to Saffo discloses a protection mask comprising a flexible hood having a head opening for placing said hood over the head of a wearer. The hood is provided with an elastic band sewn to the head opening to close the hood relatively tightly around the user's neck.

One disadvantage of Saffo, is the engagement of a non-elastic or elastic neck seal is not simply solved with the contact of the neck seal material to the neck. The elastic material must effectively seal long hair, facial hair, decorative apparel for the hair and the neck, and the overall range of anthropometric neck sizes.

The present invention replaces the standard hypoxia device by providing improved hypoxia protection, by filtering the additional cabin air required in a decompression event, and the unique feature of smoke and fire protection by providing (with or without a supply of supplemental oxygen) filtered cabin air in the event of an aircraft fire. Therefore, there exists a need for a dual air supply system providing the user or passenger with either, or both, fresh air from the local supply aircraft's emergency air source, if provided, or from the contaminated surroundings by filtering the air to remove the toxic gases before reaching the passenger. There also exists a need for a device which can rely entirely upon the ambient air supply to revive the user or passenger with fresh, breathable air from contaminated surrounding air for a temporary period sufficient to escape from the room, the surrounding area or the cabin of an aircraft.

In summary, there exists a need for an aircraft respiratory system incorporating both an oral/nasal mask providing the passenger with fresh, breathable air and a protective hood to protect the passenger from the smoke and noxious gases associated with an aircraft fire for improved passenger visibility. There also exists a need for the air purifier to continue to work after the user detaches himself from the bottled air or the aircraft's emergency air in order to exit the area, room or aircraft.

SUMMARY OF THE INVENTION

It is an object of the present invention to provide an air purifying system that allows the user to breath air from an existing air supply and/or from surrounding atmospheric air.

It is another object of the present invention to provide a protective hood to improve passengers' visibility for an escape during hypoxia and fire emergencies.

It is yet another object of the present invention to provide an oral mask and smoke hood combination which is compact and can be stored in an overhead passenger service unit of an aircraft which drops down from the service unit during an emergency. These and other objects are provided by an oral/nasal mask and hood combination.

Where provided, the mask is removably attachable to a standard oxygen supply, such as an existing oxygen supply on an aircraft overhead compartment. On aircraft without installed supplemental oxygen systems the unit may be attached to a portable oxygen supply or used without attachment to an oxygen source. The instant invention may be used for smoke and fire protection in non-aircraft environments. The mask contains a five stage filter system to allow the user to breath atmospheric air during an onboard fire or hypoxia emergency, and that protection continues after the mask is detached from the aircraft oxygen supply. Fires on aircraft can produce various products of combustion including CO, CO2, acid gases, cyanide, heat and smoke. An effective mask must reduce many of these products to tolerable levels. In the instant invention, many of these products are removed through a five stage filter. The first removes particulate smoke.

In the second stage of the filtering process, a plurality of zeolite spheres are provided for the filtering out of some toxic gases. The third stage consists of an activated charcoal carbon for the filtering out of many of the remaining gases. At this point most products of combustion would be removed, except for CO and CO2.

The fourth stage consists of a catalyst for converting carbon monoxide to carbon dioxide. This conversion significantly increases the temperature of the gas. Thus, the fifth and final stage of the filtering process consists of a heat absorber for reducing the temperature of the now breathable air to tolerable levels before reaching the user.

A hood is attached to the mask. When not in use the hood is folded compactly around filter portion of the oral/nasal mask and held in place by a retainer. A deployment strap, attached to the hood, is pulled to break the retainer when the hood is needed to be donned. The hood fits over the wearer's head, neck and shoulder area. An elastic neck seal is attached to the inside of the hood to provide a tight fit around the wearer's neck and to prevent smoke from reaching and irritating the wearer's eyes. A transparent lens, to provide visibility to the wearer during an emergency, is provided on the hood adjacent to the wearer's line of sight.

In accordance with these and other objects which will be apparent hereafter, the instant invention will now be described with particular reference to the accompanying drawings.

BRIEF DESCRIPTION OF THE DETAILED DRAWINGS

DETAILED DESCRIPTION OF THE PREFERRED EMBODIMENT

Figure 1:
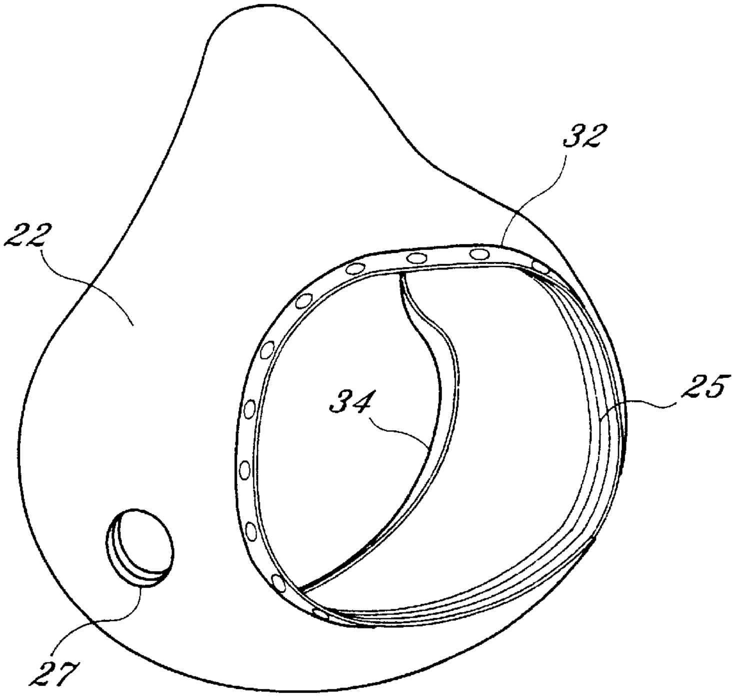
FIG. 1 is a perspective view of the oral/nasal mask.
Figure 2:
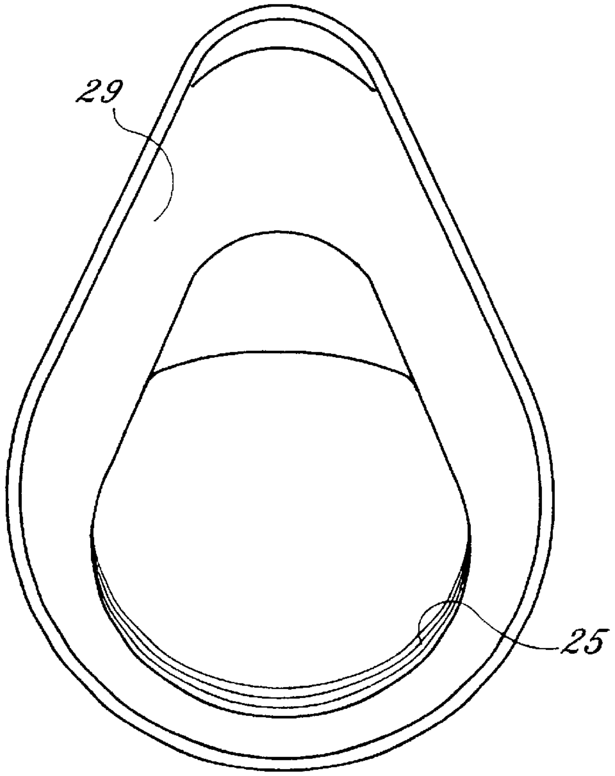
FIG. 2 is a side view of the oral/nasal mask.

An oral/nasal mask 22 of the protective hood/mask device 20 of the present invention is shown in FIGS. 1 and 2. Mask 22 has a mask inlet 32 and a mask outlet 34. Preferably, mask inlet is cylindrically shaped. Mask outlet 34 has an aperture shaped to conform to the wearer's nose and cheek region. Mask 22 also has a plurality of internal threads 25 at its mask inlet 32. An exhalation aperture 27 is located or disposed on one side of mask 22. Surface 29 at mask outlet 34 rests against the wearer's nose and cheek region to further prevent toxic gases from entering mask 22.

Figure 3:
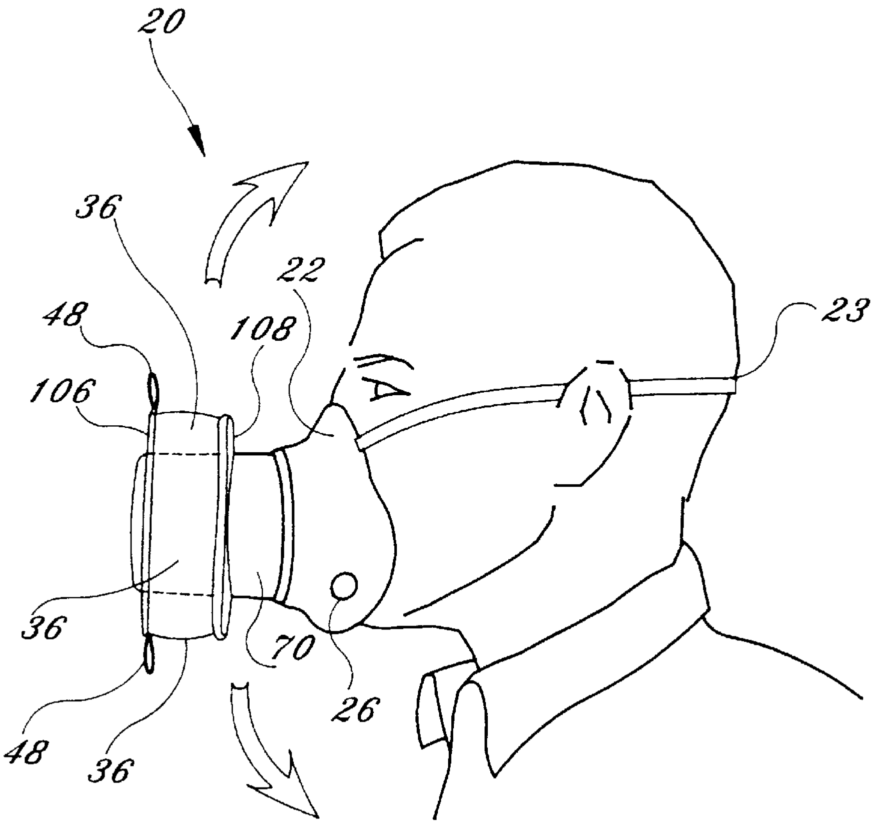
FIG. 3 is a perspective view of the oral/nasal mask-hood in use before deployment of the hood.

As seen in FIG. 3, mask 22 is shown in operation. Mask 22 is retained against the user's nose and cheek region by strap 23. Preferably, strap 23 is made of an elastic material. However, it is to be understood that any material which will retain mask 22 tightly around the user's nose and cheek region can be utilized for strap 23. A purifying assembly 66 is shown attached to mask 22. Purifying assembly 66 includes a first housing 68 and a second housing 70. Preferably housings 68 and 70 are cylindrically shaped to provide a better efficiency for assembly 66 since air flow is cylindrical. Second housing 70 contains a plurality of external threads cooperating with the internal threads 25 of mask 22. First housing 68 contains a first flange member 106 and a second flange member 108. Flanges 106 and 108 thereby form a flange recess 110. As seen in FIG. 3, a smoke hood 36 is folded compactly around the circumference of first housing 68 within flange recess 110 between flange members 106 and 108 and also retained within hood retainer 46. Attached to smoke hood 36 is at least one deployment strap 48 for pulling smoke hood 36 from its folded position. Straps 48 are pulled in the direction of the arrows A and B.

Figure 4:
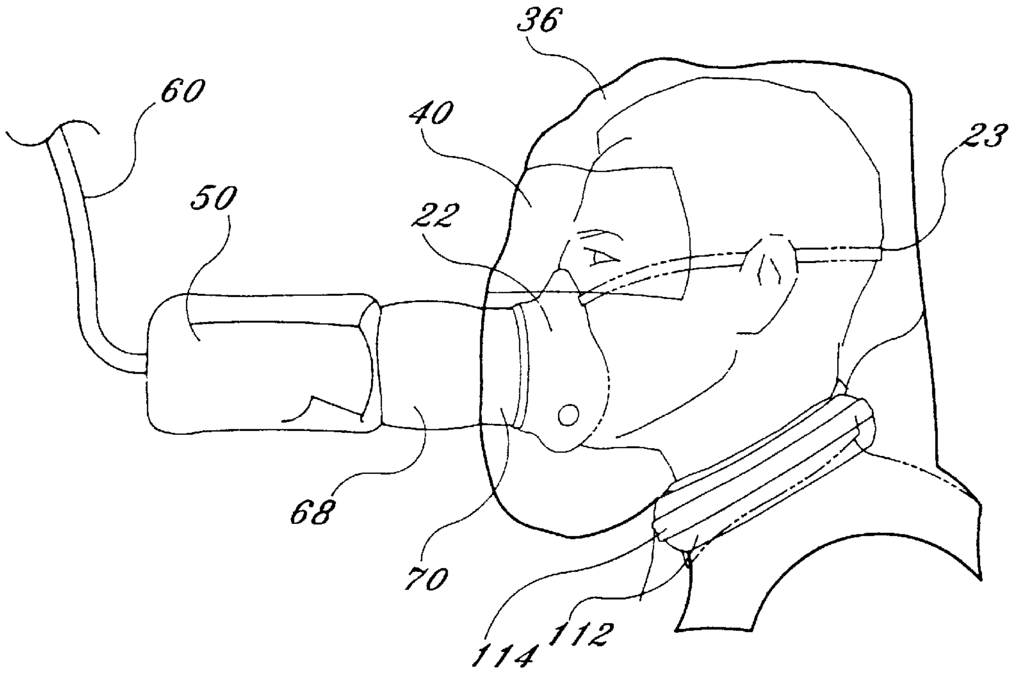
FIG. 4 is a perspective view of the oral/nasal mask-hood, attached to an existing oxygen supply, in use with the hood deployed.

FIG. 4 illustrates the protective hood/mask device 20 in operation. As in FIG. 3, mask 22 is shown positioned tightly around the user's nose and cheek area and retained by strap 23. A first end of first housing 68 is shown attached to a reservoir bag 50 which in turn is connected to air tube 60. Sized elastic rings 113 removably attach reservoir bag 50 to first housing 68. A reservoir valve assembly 52 is attached to reservoir bag 50. Reservoir valve assembly 52 includes a reservoir valve 54 fitted to reservoir bag 50 which opens under reduced internal pressure and makes possible the inhalation of ambient air if the wearer's breathing demand exceeds available oxygen volumes as supplied by the existing oxygen supply. Reservoir valve 54 is protected by reservoir protection cage 56 to assure a clear inhalation path for the ambient air. Once inside reservoir bag 50, the ambient air flows through purifying assembly 66 to provide the wearer with breathable air. Air tube 60 can be attached to an existing oxygen supply (not shown). Oxygen from the existing oxygen supply flows through air tube 60, reservoir bag 50, purifying assembly 66 and mask 22 to the wearer. Hood 36 is provided with a toroidal, elastic neck seal 112 sealed to the interior of hood 36 at 116 with a transition of the material to the opening for the head. Neck seal 112 is adjacent to a substantial portion of the user's neck area. Neck seal 112 is kept tightly around the user's neck area by elastic strip 114. Neck seal 112 has an aperture in which the user inserts his or her head through. Transparent lens 40 is sealed to the interior edge of an aperture in smoke hood 36 to provide visibility to the user during an emergency. Transparent lens 40 can be chemically treated for anti-fogging and abrasion resistance. Protective hood 36 and transparent lens 40 provide protection from direct flame, radiant heat and chemicals. As seen in FIG. 4, smoke hood 36 covers the user's head, neck and shoulder areas. Neck seal 112 prevents any outside air from locating within hood 36. Thus neck seal 112 prevents the gases from irritating the wearer's eyes.

Figure 5:
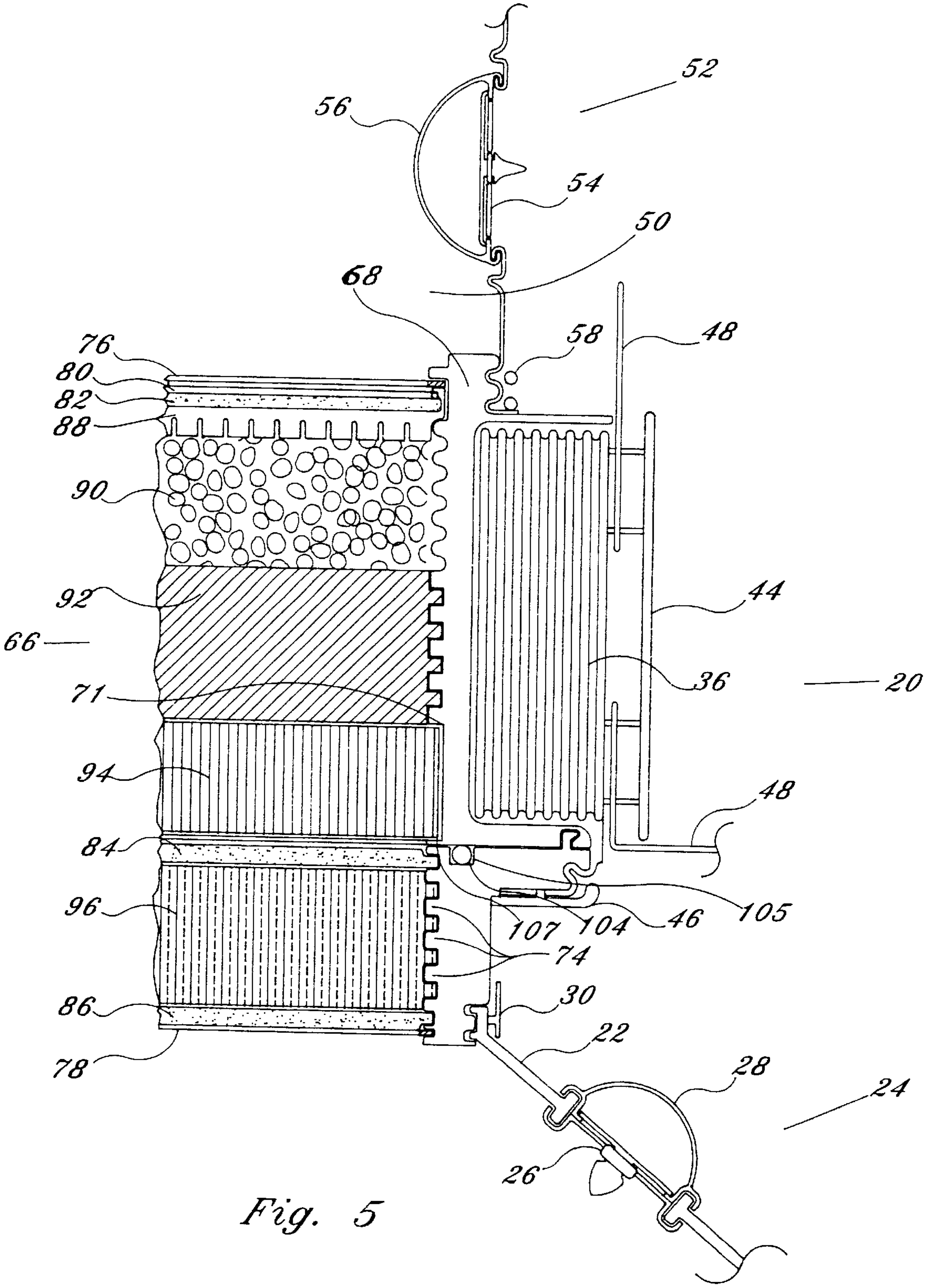
FIG. 5 is a quarter-cross section of the oral/nasal mask-hood before deployment of the hood.

As seen in FIG. 5, a quarter cross-section of hood/mask device 20 is shown. Mask 22 includes an exhalation valve assembly 24. Exhalation valve assembly 24 consists of an exhalation valve 26 for expired air and exhalation valve protective cage 28. Protective case 28 assures a clear path for the exhalations. Hood 36 is shown folded compactly between flange members 106 and 108. Hood 36 is retained folded by a thin heat shrink material 44 perforated for ease of deployment. Also attached to hood 36 are deployment straps 48 for breaking heat shrink material 44 and allowing hood 36 to unfold and be fitted and cover the head, hair, neck and shoulders of the wearer.

In addition to housings 68 and 70, purifying assembly 66 consists of a number of components located within housings 68 and 70. Located within housing 70 is a heat absorber 96. Preferably, heat absorber is molded into a cylindrical configuration similar to housing 70. Heat absorber can be any material which reduces the temperature of the gases flowing through housing 70 before they reach the wearer. Heat absorber 96 consists of microencapsulated phase change materials which reduce the temperature of inhaled gases to a limit below that of human skin or tissue damage. Heat absorber 96 has a plurality of external threads 100 for mating with internal threads 74 of housing 70. Threads 100 and 74 prevent sidewall channeling of the gases through housing 70. Threads 74 and 100 create a turbulence path along the sides of heat absorber 96 to prevent gases from flowing through. Thus, this unique mating method protects the wearer from breathing gases of high temperatures which would have traveled through housing 70 without going through heat absorber 96. Filters 84 and 86 are provided at each end of heat absorber 96. Filters 84 and 86 retain filtration media that are present at each end of heat absorber 96. A snap ring 78 is provided at the second end of housing 70 to maintain a tight fit for filters 84 and 86 with heat absorber 96.

Located within housing 68 is a three stage air purifier. A filter 82 and inlet screen 88 are present at the first end of housing 68. In the second stage, a plurality of zeolite molecular sieves in the form of spheres or one piece monolith 90 are provided in an internal ridged surface section 73 of housing 68. Ridges 73 eliminate sidewall gas channeling along the interface between housing and zeolite structures 90. Zeolite material filters out some of the combustion products flowing into housing 68 such as acid gases and water vapor.

In the third stage, an immobilized activated carbon monolith 92 is provided. Preferably, activated carbon 92 is cylindrically shaped similar to housing 68. Activated carbon 92 contains a plurality of external threads 98 for mating with internal threads 72 of housing 68. Threads 72 and 98 prevent sidewall channeling of the gases through housing 68 by creating a turbulence path along the sides activated carbon 92 to prevent gases from flowing through. Thus, this mating method protects the wearer from breathing toxic and noxious gases which would have traveled through housing 68 without going through activated carbon 92. Activated carbon 92 can be comprised of an activated charcoal consisting of irregular shaped immobilized grains. The grains are impregnated with copper, silver and chromium for holding back and filtering gases which were able to pass through zeolite spheres 90 namely, hydrocarbons, water vapor, hydrogen bromide, hydrogen fluoride, hydrogen chloride, hydrogen cyanide, sulphur dioxide, oxides of nitrogen, acrolein and ammonia. After the gas has been filtered through activated carbon 92 the only combustion products remaining in abundance are CO and heat.

In its fourth stage, a catalyst 94, typically a noble metal monolith, is provided for oxidizing the toxic carbon monoxide gas to carbon dioxide. This conversion of the gas also increases the temperature of the gas. Preferably, catalyst 94 is cylindrically shaped similar to housing 68. Catalyst 94 can be either formed from a mixture of transition metal oxides commonly known as hopcalite or result from the coating or plating of elements from the platinum metal group on a ceramic substrate. Catalyst 94 snaps into housing 68 between first housing internal thread 71 and first housing internal flange 107. This snap-in construction prevents side wall channeling of the toxic carbon monoxide out of first housing 68 and into second housing 70. A filter retainer 80 and snap ring 76 are provided at the first end of housing 68 to maintain a tight fit between filter 82, screen 88, spheres 90, activated carbon 92 and catalyst 94. In addition spheres 90 are tightly retained between screen 88 and activated carbon 92. After the gas has been converted to carbon dioxide it travels to second housing 70 to heat absorber 96 which reduces the temperature of the gas as described above.

Figure 6:
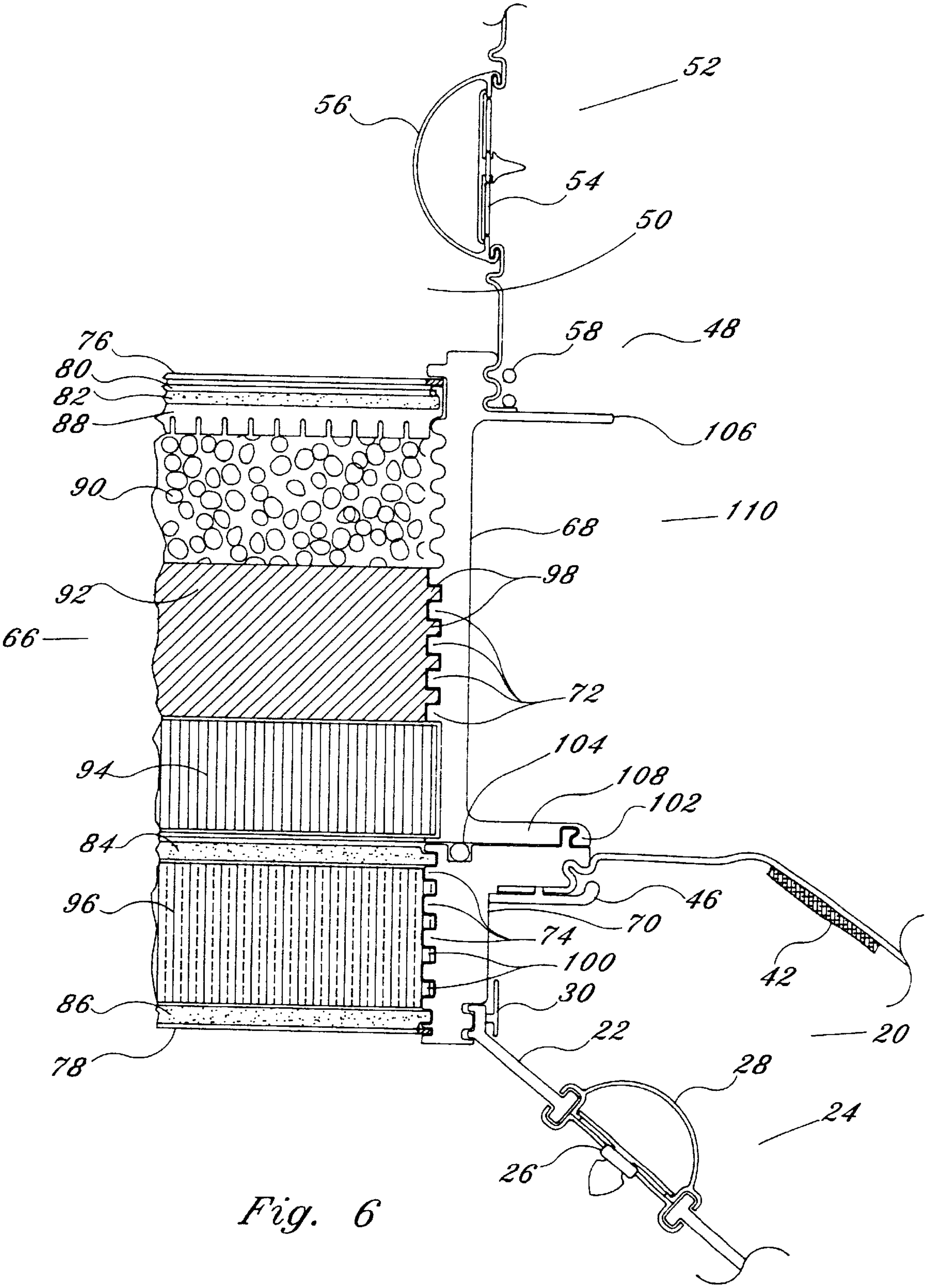
FIG. 6 is a quarter-cross section of the oral/nasal mask-hood after deployment of the hood.

Housings 68 and 70 are attached to each other by snap lock 102. Housing 70 contains a recess 105. A sealing ring 104 is provided and located within recess 105 to prevent gases from channeling through the area where housings 68 and 70 meet and thus avoiding the filtering stages. As seen in FIG. 6, smoke hood 36 is shown deployed (Deployment straps 48 have been pulled and heat shrink material 44 has been broken). Smoke hood 36 remains retained within hood retainer 46. Thin layers of anti-fogging desiccant material 42 are attached to the interior surface of hood 36 immediately adjacent to mask exhalation valve 26. Therefore the expired air traveling through valve 26 contacts desiccant material 42 which prevents the air from fogging transparent lens 40. Neck seal 112 in conjunction with hood 36 define a closed space which is inflated by the wearer's exhalations. Therefore, the inflated hood enhances thermal protection and creates a cushion for the wearer's head in the case of falling objects hitting hood 36. In addition, the confined exhalations provide a secondary source of breathable gas for penultimate escape efforts in fire emergencies.

Figure 7:
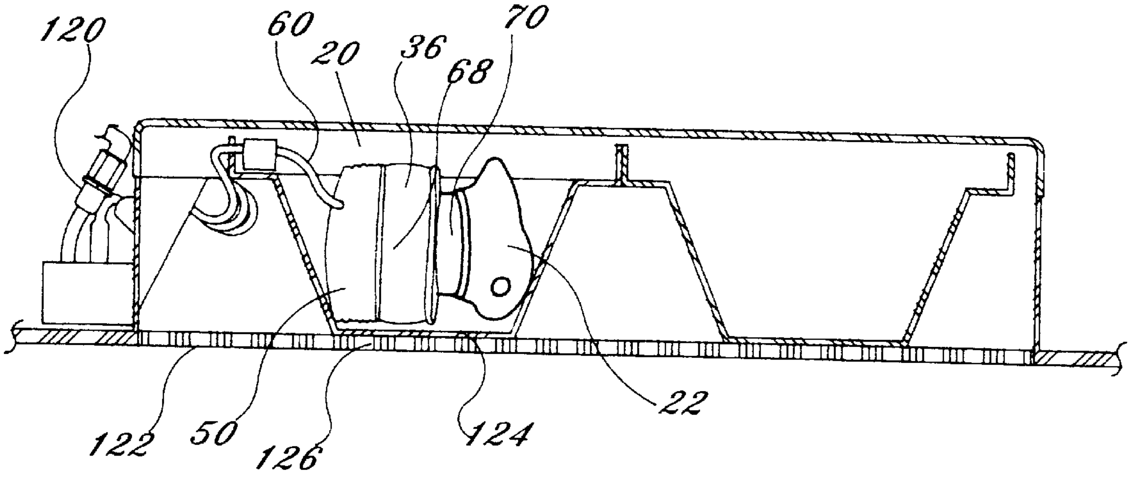
FIG. 7 is a perspective view of the oral/nasal mask-hood stored in an overhead compartment of an aircraft.

As seen in FIG. 7, the protective hood/mask device 20 is shown stored in its initial compact position within storage compartment 122. Smoke hood 36 is folded around the circumference of first housing 68. Smoke hood 36 is constructed of a non-flammable, gas impermeable material. Reservoir bag 50 is folded into a compact position next to device 20. Air tube 60 is shown attached at one end to reservoir bag 50 and at its other end to existing oxygen supply 120. Device 20 can be stored in a container 124 to protect device 20 from the containments located within compartment 122.

While the instant invention has been described in what is considered to be the preferred embodiment, it is to be understood that these descriptions are given by means of example only, and not by means of limitation. It is to be understood that changes and modifications may be made to the description given and still be within the scope of the invention. Additionally, the instant invention is not limited to aircraft emergency, but can be used in fire and hypoxia emergencies occurring in other situations as well. Further, it is clear that obvious changes and modifications will occur to those skilled in the art.

We claim:

1. A device for protection to a user, from heat, noxious and/or toxic gases during hypoxic and fire emergencies, the device usable alone or the device usable in conjunction with a breathable oxygen source comprising:

an exclusively dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

wherein said device provides protection to a user, from heat, noxious and/or toxic gases which might be present during hypoxic and fire emergencies;

a hood constructed of a non-flammable, gas impermeable material, said hood covering a user's head and neck area, said hood having an interior surface and an exterior surface, said means for converting attached to said hood;

means for viewing during hypoxic and fire emergencies attached to said hood and disposed substantially in front of a user's eyes;

means for preventing fogging of said means for viewing during exhalation by said user, said means for preventing fogging disposed on said hood and is adjacent said exhalation valve when said hood is properly deployed; and means for preventing said atmospheric air from locating within said hood, said means for preventing attached to said interior surface of said hood.

2. The device of claim 1, wherein said means for preventing is a non-permeable, flexible neck seal, said neck seal having a neck seal aperture to allow a user's head area to be inserted through said aperture, said neck seal shaped to allow said neck seal to be adjacent to a substantial portion of a user's neck area, said neck seal aperture having an elastic edge to tightly seal said neck seal around said substantial portion of the user's neck area.

3. The device of claim 1, wherein said means for retaining is an elastic strap attached to said mask, whereby a portion of a user's head is inserted through said strap thereby allowing said strap to be wrapped around the user's head.

4. The device of claim 1, wherein said means for coverting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member.

5. The device of claim 4 wherein said means for converting further comprises a screen disposed within said housing member intermediate the first end of said housing member and said means for filtering.

6. The device of claim 1, wherein said hood is further constructed of a flexible material to allow said hood to be folded compactly around said means for converting.

7. The device of claim 6, further comprising a heat shrink material disposed around said hood to keep said hood folded compactly around said means for converting, and a deployment strap to release said hood from its compact position.

8. The device of claim 1, wherein said device is stored in a standard overhead oxygen mask aircraft compartment during non-emergency situations.

9. A device for protection to a user, from heat, noxious and/or toxic gases during hypoxic and fire emergencies, the device used alone or the device is used in conjunction with a breathable oxygen source comprising:

a dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

a hood constructed of a non-flammable, gas impermeable material, said hood covering a user's head and neck area, said hood having an interior surface and an exterior surface, said means for converting attached to said hood;

means for viewing during said hypoxic and fire emergencies attached to said hood and disposed substantially in front of a user's eyes;

means for preventing fogging of said means for viewing during exhalation by said user; and means for preventing said atmospheric air from locating within said hood, said means for preventing attached to said interior surface of said hood;

wherein said means for viewing comprises a transparent member attached to said hood substantially in front of a user's eyes, said transparent member constructed of a rigid material, wherein said means for preventing fogging is a desiccant material attached to said hood and disposed adjacent to said exhalation valve.

10. A device for protection to a user, from heat, noxious and/or toxic gases during hypoxic and fire emergencies, the device usable alone or the device usable in conjunction with a breathable oxygen source comprising:

an exclusively dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

wherein said device provides protection to a user, from heat, noxious and/or toxic gases which might be present during hypoxic and fire emergencies;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member;

wherein said means for converting further comprises a screen disposed within said housing member intermediate the first end of said housing member and said means for filtering;

wherein said means for converting further comprises a plurality of filters, a first of said plurality of filters located within said housing member intermediate said screen and the first end of said housing member, a second of said plurality of filters located within said housing member intermediate said means for reducing and said means for oxidating, a third of said plurality of filters located within said housing member intermediate said means for reducing and the second end of said housing member.

11. A device for protection to a user, from heat, noxious and/or toxic gases during hypoxic and fire emergencies, the device usable alone or the device usable in conjunction with a breathable oxygen source comprising:

an exclusively dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

wherein said device provides protection to a user, from heat, noxious and/or toxic gases which might be present during hypoxic and fire emergencies;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member;

wherein said means for filtering comprises:

an immobilized activated carbon monolith disposed within said housing member intermediate said means for oxidating and the first end of said housing member; and a plurality of zeolite molecular sieves located within said housing member intermediate said carbon monolith and the first end of said housing member.

12. A device for protection to a user, from heat, noxious and/or toxic gases during hypoxic and fire emergencies, the device used alone or the device is used in conjunction with a breathable oxygen source comprising:

a dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve; and means for retaining said mask tightly on a user's mouth and nose regions at said second mask aperture, said means for retaining connected to said mask;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member;

wherein said means for filtering comprises:

an immobilized activated carbon monolith disposed within said housing member intermediate said means for oxidating and the first end of said housing member;

a plurality of zeolite molecular sieves located within said housing member intermediate said carbon monolith and the first end of said housing member;

wherein said carbon monolith having a plurality of external threads cooperating with internal threads of said housing member to help prevent sidewall channeling of said gases.

13. A device for protection to a user, from heat, noxious and/or toxic gases during hypoxic and fire emergencies, the device usable alone or the device usable in conjunction with a breathable oxygen source comprising:

an exclusively dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

wherein said device provides protection to a user, from heat, noxious and/or toxic gases which might be present during hypoxic and fire emergencies;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member;

wherein said means for oxidating is a catalyst monolith.

14. The device of claim 13, wherein said catalyst monolith is attached to an internal wall of said housing member to prevent sidewall channeling of said gases.

15. A device for protection to a user, from heat, noxious and/or toxic gases during hypoxic and fire emergencies, the device usable alone or the device usable in conjunction with a breathable oxygen source comprising:

an exclusively dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

wherein said device provides protection to a user, from heat, noxious and/or toxic gases which might be present during hypoxic and fire emergencies;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member;

wherein said means for reducing is a molded heat absorber.

16. A device for protection to a user, from heat, noxious and/or toxic gases during hypoxic and fire emergencies, the device used alone or the device is used in conjunction with a breathable oxygen source comprising:

a dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve; and means for retaining said mask tightly on a user's mouth and nose regions at said second mask aperture, said means for retaining connected to said mask;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member; and means for reducing the temperature of said inhaled gases, said means for reducing disposed within said housing member intermediate said means for oxidating and the second end of said housing member;

wherein said means for reducing is a molded heat absorber;

wherein said heat absorber having a plurality of external threads cooperating with internal threads of said housing member to help prevent sidewall channeling of said gases.

17. A device for protection to a user, from heat, noxious and/or toxic gases during hypoxic and fire emergencies, the device usable alone or the device usable in conjunction with a breathable oxygen source comprising:

an exclusively dry multi-stage filtering means for converting atmospheric gases into breathable air;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

wherein said device provides protection to a user, from heat, noxious and/or toxic gases which might be present during hypoxic and fire emergencies;

wherein said means for converting comprises:

a housing member having a first end and a second end;

means for filtering said inhaled gases disposed within said housing member;

means for oxidating toxic carbon monoxide to carbon dioxide disposed within said housing member intermediate said means for filtering and the second end of said housing member;

means for reducing the temperature of said inhaled gases, said means for reducing disposed within said housing member intermediate said means for oxidating and the second end of said housing member;

a detachable oxygen reservoir bag attached to said first end of said first housing, said reservoir bag having an ambient air valve to receive ambient air; and an air tube attached at a first end to said reservoir bag and at a second end adaptable to be attached to said breathable oxygen source;

wherein said breathable oxygen source is an aircraft's emergency oxygen supply.

18. A device for protection to a user, from heat, noxious and/or toxic gases during hypoxic and fire emergencies, the device used alone or the device is used in conjunction with a breathable oxygen source comprising:

a hood constructed of a non-flammable, gas impermeable material, said hood covering a user's head and neck area, said hood having an interior surface and an exterior surface;

a dry multi-stage filtering means for converting atmospheric gases into breathable air, said means for converting attached to said hood;

a mask having a first and second mask aperture, said mask constructed and arranged to conform to the contours of a user's mouth and nose region, said mask connected to said means for converting at said first mask aperture, said mask having an exhalation valve;

means for retaining said mask tightly on a user's mouth and nose regions at said second mask aperture, said means for retaining connected to said mask;

means for viewing during hypoxic and fire emergencies attached to said hood and disposed substantially in front of a user's eyes;

means for preventing fogging of said means for viewing during exhalation by said users, said means for preventing fogging disposed on said hood and is adjacent said exhalation valve when said hood is properly deployed; and means for preventing said atmospheric air from locating within said hood, said means for preventing attached to said interior surface of said hood.

19. A device for protection to a user, from heat, noxious and/or toxic gases during hypoxic and fire emergencies, the device used alone or the device is used in conjunction with a breathable oxygen source comprising:

a hood constructed of a non-flammable, gas impermeable material, said hood covering a user's head and neck area, said hood having an interior and exterior surface;

a dry multi-stage filtering means for converting atmospheric gases into breathable air, said means for converting attached to said hood;

means for preventing the atmospheric gases from bypassing said dry filtering means;

a mask having a first and second mask aperture, said mask constructed and arranged to conform to the contours of a user's mouth and nose region, said mask connected to said means for converting at said first mask aperture, said mask having an escalation valve;

means for retaining said mask tightly on a user's mouth and nose regions at said second mask aperture, said means for retaining connected to said mask;

a rigid transparent member for viewing during hypoxic and fire emergencies attached to said hood and disposed substantially in front of a user's eyes;

an anti-fogging desiccant material attached to the interior surface of said hood and disposed adjacent to said exhalation valve, said desiccant material preventing the exhaled air from fogging said transparent member; and means for preventing said atmospheric air from locating within said hood, said means for preventing attached to said interior surface of said hood.

* * * * *